(12) United States Patent
Fu et al.

(10) Patent No.: US 10,174,298 B2
(45) Date of Patent: Jan. 8, 2019

(54) NICOTINAMIDE PHOSPHORIBOSYLTRANSFERASE (NAMPT) MUTANT AND USE THEREOF

(71) Applicant: BONTAC BIO-ENGINEERING(SHENZHEN) CO., LTD, Shenzhen (CN)

(72) Inventors: Rongzhao Fu, Shenzhen (CN); Qi Zhang, Shenzhen (CN)

(73) Assignee: BONTAC BIO-ENGINEERING(SHENZHEN) CO., LTD, Shenzhen (CN)

( * ) Notice: Subject to any disclaimer, the term of this patent is extended or adjusted under 35 U.S.C. 154(b) by 0 days.

(21) Appl. No.: 15/574,849

(22) PCT Filed: Jul. 30, 2016

(86) PCT No.: PCT/CN2016/092456
§ 371 (c)(1),
(2) Date: Nov. 17, 2017

(87) PCT Pub. No.: WO2018/023206
PCT Pub. Date: Feb. 8, 2018

(65) Prior Publication Data
US 2018/0230443 A1 Aug. 16, 2018

(51) Int. Cl.
*C12N 9/10* (2006.01)
*C12P 19/30* (2006.01)

(52) U.S. Cl.
CPC .............. *C12N 9/1077* (2013.01); *C12N 9/10* (2013.01); *C12P 19/30* (2013.01); *C12Y 204/02012* (2013.01)

(58) Field of Classification Search
CPC ......... C12P 7/6409; C12P 5/026; C12P 19/30; C11B 1/104; C07C 7/10; C07C 11/18; C12N 9/1077; C12N 9/10; C12Y 204/02012
See application file for complete search history.

(56) References Cited

FOREIGN PATENT DOCUMENTS

| CN | 101914614 A | 12/2010 |
|---|---|---|
| CN | 103710321 A | 4/2014 |
| CN | 103961691 A | 8/2014 |
| WO | 2012024478 A2 | 2/2012 |

OTHER PUBLICATIONS

Kim et al., J. Mol. Biol. 362:66-77, 2006.*
Witkowski et al., Biochemistry 38:11643-11650, 1999.*
Tang et al., Phil Trans R Soc B 368:20120318, 1-10, 2013.*
Seffernick et al., J. Bacteriol. 183(8):2405-2410, 2001.*
Branden et al., Introduction to Protein Structure, Garland Publishing Inc., New York, p. 247, 1991.*
Sadowski et al., Current Opinion in Structural Biology 19:357-362, 2009.*
Accession No. WP_013015090.1, nicotinate phosphoribosyltransferase[Meiothermus ruber], NCBO GenBank. May 26, 2013.
Feng Wang et al, Enzymatic activities of recombinant human NAMPT and NAMPT(H247A) proteins, Dec. 31, 2011, Issue No. 2, vol. 40, p. 156-162.
Peng Liu et al, Regulation of Inflammatory Cytokine Expression in Pulmonary Epithelial Cells by Pre-B-cell Colony-enhancing Factor via a Nonenzymatic and AP-1-dependent Mechanism. The Journal of Biological Chemistry. Oct. 2, 2009,Issue No. 40, vol. No. 284, p. 27344-27351.
Tao Wang et al Structure of Nampt PBEF visfatin, a mammalian NAD biosynthetic enzyme. Nature Structural & Molecuiar Biology, Jun. 18, 2006, Issue No. 7, vol. No. 13, p. 661-662.

* cited by examiner

*Primary Examiner* — Delia M Ramirez
(74) *Attorney, Agent, or Firm* — Gokalp Bayramoglu

(57) ABSTRACT

The present invention discloses a Nicotinamide phosphoribosyltransferase (nampt) mutant and use thereof. The present invention relates to a nicotinamide phosphoribosyltransferase (Nampt) mutant artificially obtained through genic site-directed mutation. An object of the present invention is to provide a Nampt mutant having a catalytic activity higher than that of a conventional wild type parent, wherein the enzymatic activity of the Nampt mutant provided in the present invention is 1.2-6.9 times of the enzymatic activity of the parent.

3 Claims, No Drawings
Specification includes a Sequence Listing.

SEQUENCE LISTING

```
<160> NUMBER OF SEQ ID NOS: 29

<210> SEQ ID NO 1
<211> LENGTH: 1392
<212> TYPE: DNA
<213> ORGANISM: Unknown
<220> FEATURE:
<223> OTHER INFORMATION: Meiothermus ruber DSM 1279

<400> SEQUENCE: 1
atgaaaaccc tcaaccccca caacctcatc ctcaacaccg acagctacaa agccagtcac        60
tttgcccagt tccccaaagg catgacctat gccagttggt acatcgagag ccggggcggc       120
gactcgaatt ttgtgcgttt ctttggccta caggccttct taatcgagta cctcagcaaa       180
ggggtcagcc tggccgatgt ggaggaggcc caggaagttt tcctggccca cggcctgccc       240
ttccccacag aaggctggcg ctacatcgct caggacttag gagggcggct gccggtgcgc       300
atccgggccg tgcccgaggg taaggtggtt cccgtacaca accccctggt catcatcgag       360
agcaccgacc ccaaagtgcc ctggctgccg ggttggctcg agaccgcgct gctgcgggcg       420
gtctggtacc ccaccacggt ctgcacggtc tcctggggta tccgcaacac catcaaggag       480
tacctggaga aaaccgccga cgaccccgag gccgagctgc ccttcaagct gcacgacttt       540
ggcgcgcgcg gggtgagcag cctcgagagc gccgggctgg gcgggatggc ccacctggtg       600
aactttatgg gcaccgacac cgtcaccgcc ctgatctacg cccgcaacta ctacggggcc       660
gagatggccg gctacagcat cccggccatg gagcacagca ccgtgaccag ctttggccgc       720
accggcgagg cccaggccta ccgccagatg ctcgagacct tgccaagcc gggggccctg       780 atggccatgg tgattgattc gtacaaccgc gagcacgccg tgggccagat tatcggcgaa       840
gaactgcgcg agctcatcca gcagtcgggg gccaccgtgg tcatccggcc cgactcgggc       900
gacccgccct tcgtggtgct gcgcaccgtg cagaccctcg aggccaaatt tggcgccacc       960
ctcaaccgca agggctacaa ggtgctgaac ggggtgcggg tcatccaggg cgatggggtg      1020
aacgccgact ccatccgcaa ggtgctgttt ttgctcgagc agtggggcta cagcgcctcc      1080
aacgtggcct tcggcatggg cggggccctc ttgcagcacc cccaccgcga tacccagaag      1140
ttcgcccaga agctgcacct ggtcacggtg aacggcgaga cctacggggt gggcaagagc      1200
ccggtggacg accccggcaa actctccaag aagggccgtc tggacgttat ccaggacgag      1260
cgcggcatcc gcacggtgga gctgccgctg gaggccgccc agccgcaccc ccagagcatc      1320
ctgcaaaccg tattcgagaa cgggtcgatt acccggcgct acacctggga agaggtgcgc      1380
aacaacgctt ag                                                          1392

<210> SEQ ID NO 2
<211> LENGTH: 463
<212> TYPE: PRT
<213> ORGANISM: Unknown
```

-continued

```
<220> FEATURE:
<223> OTHER INFORMATION: Meiothermus ruber DSM 1279

<400> SEQUENCE: 2

Met Lys Thr Leu Asn Pro His Asn Leu Ile Leu Asn Thr Asp Ser Tyr
1               5                   10                  15

Lys Ala Ser His Phe Ala Gln Phe Pro Lys Gly Met Thr Tyr Ala Ser
            20                  25                  30

Trp Tyr Ile Glu Ser Arg Gly Gly Asp Ser Asn Phe Val Arg Phe Phe
        35                  40                  45

Gly Leu Gln Ala Phe Leu Ile Glu Tyr Leu Ser Lys Gly Val Ser Leu
    50                  55                  60

Ala Asp Val Glu Glu Ala Gln Glu Val Phe Leu Ala His Gly Leu Pro
65                  70                  75                  80

Phe Pro Thr Glu Gly Trp Arg Tyr Ile Ala Gln Asp Leu Gly Gly Arg
                85                  90                  95

Leu Pro Val Arg Ile Arg Ala Val Pro Glu Gly Lys Val Val Pro Val
            100                 105                 110

His Asn Pro Leu Val Ile Ile Glu Ser Thr Asp Pro Lys Val Pro Trp
        115                 120                 125

Leu Pro Gly Trp Leu Glu Thr Ala Leu Leu Arg Ala Val Trp Tyr Pro
    130                 135                 140

Thr Thr Val Cys Thr Val Ser Trp Gly Ile Arg Asn Thr Ile Lys Glu
145                 150                 155                 160

Tyr Leu Glu Lys Thr Ala Asp Asp Pro Glu Ala Glu Leu Pro Phe Lys
                165                 170                 175

Leu His Asp Phe Gly Ala Arg Gly Val Ser Ser Leu Glu Ser Ala Gly
            180                 185                 190

Leu Gly Gly Met Ala His Leu Val Asn Phe Met Gly Thr Asp Thr Val
        195                 200                 205

Thr Ala Leu Ile Tyr Ala Arg Asn Tyr Tyr Gly Ala Glu Met Ala Gly
    210                 215                 220

Tyr Ser Ile Pro Ala Met Glu His Ser Thr Val Thr Ser Phe Gly Arg
225                 230                 235                 240

Thr Gly Glu Ala Gln Ala Tyr Arg Gln Met Leu Glu Thr Phe Ala Lys
                245                 250                 255

Pro Gly Ala Leu Met Ala Met Val Ile Asp Ser Tyr Asn Arg Glu His
            260                 265                 270

Ala Val Gly Gln Ile Ile Gly Glu Glu Leu Arg Glu Leu Ile Gln Gln
        275                 280                 285

Ser Gly Ala Thr Val Val Ile Arg Pro Asp Ser Gly Asp Pro Pro Phe
    290                 295                 300

Val Val Leu Arg Thr Val Gln Thr Leu Glu Ala Lys Phe Gly Ala Thr
305                 310                 315                 320

Leu Asn Arg Lys Gly Tyr Lys Val Leu Asn Gly Val Arg Val Ile Gln
                325                 330                 335

Gly Asp Gly Val Asn Ala Asp Ser Ile Arg Lys Val Leu Phe Leu Leu
            340                 345                 350

Glu Gln Trp Gly Tyr Ser Ala Ser Asn Val Ala Phe Gly Met Gly Gly
        355                 360                 365

Ala Leu Leu Gln His Pro His Arg Asp Thr Gln Lys Phe Ala Gln Lys
    370                 375                 380

Leu His Leu Val Thr Val Asn Gly Glu Thr Tyr Gly Val Gly Lys Ser
385                 390                 395                 400
```

```
Pro Val Asp Asp Pro Gly Lys Leu Ser Lys Lys Gly Arg Leu Asp Val
            405                 410                 415

Ile Gln Asp Glu Arg Gly Ile Arg Thr Val Glu Leu Pro Leu Glu Ala
            420                 425                 430

Ala Gln Pro His Pro Gln Ser Ile Leu Gln Thr Val Phe Glu Asn Gly
            435                 440                 445

Ser Ile Thr Arg Arg Tyr Thr Trp Glu Glu Val Arg Asn Asn Ala
    450                 455                 460

<210> SEQ ID NO 3
<211> LENGTH: 463
<212> TYPE: PRT
<213> ORGANISM: Artificial Sequence
<220> FEATURE:
<223> OTHER INFORMATION: F180A mutant

<400> SEQUENCE: 3

Met Lys Thr Leu Asn Pro His Asn Leu Ile Leu Asn Thr Asp Ser Tyr
1               5                   10                  15

Lys Ala Ser His Phe Ala Gln Phe Pro Lys Gly Met Thr Tyr Ala Ser
            20                  25                  30

Trp Tyr Ile Glu Ser Arg Gly Gly Asp Ser Asn Phe Val Arg Phe Phe
        35                  40                  45

Gly Leu Gln Ala Phe Leu Ile Glu Tyr Leu Ser Lys Gly Val Ser Leu
    50                  55                  60

Ala Asp Val Glu Glu Ala Gln Glu Val Phe Leu Ala His Gly Leu Pro
65                  70                  75                  80

Phe Pro Thr Glu Gly Trp Arg Tyr Ile Ala Gln Asp Leu Gly Gly Arg
                85                  90                  95

Leu Pro Val Arg Ile Arg Ala Val Pro Glu Gly Lys Val Val Pro Val
            100                 105                 110

His Asn Pro Leu Val Ile Ile Glu Ser Thr Asp Pro Lys Val Pro Trp
            115                 120                 125

Leu Pro Gly Trp Leu Glu Thr Ala Leu Leu Arg Ala Val Trp Tyr Pro
    130                 135                 140

Thr Thr Val Cys Thr Val Ser Trp Gly Ile Arg Asn Thr Ile Lys Glu
145                 150                 155                 160

Tyr Leu Glu Lys Thr Ala Asp Asp Pro Glu Ala Glu Leu Pro Phe Lys
                165                 170                 175

Leu His Asp Ala Gly Ala Arg Gly Val Ser Ser Leu Glu Ser Ala Gly
            180                 185                 190

Leu Gly Gly Met Ala His Leu Val Asn Phe Met Gly Thr Asp Thr Val
    195                 200                 205

Thr Ala Leu Ile Tyr Ala Arg Asn Tyr Tyr Gly Ala Glu Met Ala Gly
    210                 215                 220

Tyr Ser Ile Pro Ala Met Glu His Ser Thr Val Thr Ser Phe Gly Arg
225                 230                 235                 240

Thr Gly Glu Ala Gln Ala Tyr Arg Gln Met Leu Glu Thr Phe Ala Lys
                245                 250                 255

Pro Gly Ala Leu Met Ala Met Val Ile Asp Ser Tyr Asn Arg Glu His
            260                 265                 270

Ala Val Gly Gln Ile Ile Gly Glu Glu Leu Arg Glu Leu Ile Gln Gln
        275                 280                 285

Ser Gly Ala Thr Val Val Ile Arg Pro Asp Ser Gly Asp Pro Pro Phe
    290                 295                 300
```

Val Val Leu Arg Thr Val Gln Thr Leu Glu Ala Lys Phe Gly Ala Thr
305                 310                 315                 320

Leu Asn Arg Lys Gly Tyr Lys Val Leu Asn Gly Val Arg Val Ile Gln
            325                 330                 335

Gly Asp Gly Val Asn Ala Asp Ser Ile Arg Lys Val Leu Phe Leu Leu
            340                 345                 350

Glu Gln Trp Gly Tyr Ser Ala Ser Asn Val Ala Phe Gly Met Gly Gly
            355                 360                 365

Ala Leu Leu Gln His Pro His Arg Asp Thr Gln Lys Phe Ala Gln Lys
            370                 375                 380

Leu His Leu Val Thr Val Asn Gly Glu Thr Tyr Gly Val Gly Lys Ser
385                 390                 395                 400

Pro Val Asp Asp Pro Gly Lys Leu Ser Lys Lys Gly Arg Leu Asp Val
                405                 410                 415

Ile Gln Asp Glu Arg Gly Ile Arg Thr Val Glu Leu Pro Leu Glu Ala
                420                 425                 430

Ala Gln Pro His Pro Gln Ser Ile Leu Gln Thr Val Phe Glu Asn Gly
                435                 440                 445

Ser Ile Thr Arg Arg Tyr Thr Trp Glu Glu Val Arg Asn Asn Ala
    450                 455                 460

<210> SEQ ID NO 4
<211> LENGTH: 36
<212> TYPE: DNA
<213> ORGANISM: Artificial Sequence
<220> FEATURE:
<223> OTHER INFORMATION: the sequence is synthetized

<400> SEQUENCE: 4
gttcaaactg cacgacgcgg gtgctcgtgg tgtttc                              36

<210> SEQ ID NO 5
<211> LENGTH: 36
<212> TYPE: DNA
<213> ORGANISM: Artificial Sequence
<220> FEATURE:
<223> OTHER INFORMATION: the sequence is synthetized

<400> SEQUENCE: 5
gaaacaccac gagcacccgc gtcgtgcagt ttgaac                              36

<210> SEQ ID NO 6
<211> LENGTH: 36
<212> TYPE: DNA
<213> ORGANISM: Artificial Sequence
<220> FEATURE:
<223> OTHER INFORMATION: the sequence is synthetized

<400> SEQUENCE: 6
gttcaaactg cacgactggg gtgctcgtgg tgtttc                              36

<210> SEQ ID NO 7
<211> LENGTH: 36
<212> TYPE: DNA
<213> ORGANISM: Artificial Sequence
<220> FEATURE:
<223> OTHER INFORMATION: the sequence is synthetized

<400> SEQUENCE: 7
gaaacaccac gagcaccccca gtcgtgcagt ttgaac                             36

<210> SEQ ID NO 8
<211> LENGTH: 40
<212> TYPE: DNA
<213> ORGANISM: Artificial Sequence
<220> FEATURE:
<223> OTHER INFORMATION: the sequence is synthetized

<400> SEQUENCE: 8
caaactgcac gacttcggtt atcgtggtgt ttcttctctg                          40

<210> SEQ ID NO 9
<211> LENGTH: 40
<212> TYPE: DNA
<213> ORGANISM: Artificial Sequence
<220> FEATURE:
<223> OTHER INFORMATION: the sequence is synthetized

<400> SEQUENCE: 9
cagagaagaa acaccacgat aaccgaagtc gtgcagtttg                          40

<210> SEQ ID NO 10
<211> LENGTH: 31
<212> TYPE: DNA
<213> ORGANISM: Artificial Sequence
<220> FEATURE:
<223> OTHER INFORMATION: the sequence is synthetized

<400> SEQUENCE: 10
ctatcccggc tatggcgcac tctaccgtta c                                   31

<210> SEQ ID NO 11
<211> LENGTH: 31
<212> TYPE: DNA
<213> ORGANISM: Artificial Sequence
<220> FEATURE:
<223> OTHER INFORMATION: the sequence is synthetized

<400> SEQUENCE: 11
gtaacggtag agtgcgccat agccgggata g                                   31

<210> SEQ ID NO 12
<211> LENGTH: 34
<212> TYPE: DNA
<213> ORGANISM: Artificial Sequence
<220> FEATURE:
<223> OTHER INFORMATION: the sequence is synthetized

<400> SEQUENCE: 12
ctctatcccg gctatgcagc actctaccgt tacc                                34

<210> SEQ ID NO 13
<211> LENGTH: 34
<212> TYPE: DNA
<213> ORGANISM: Artificial Sequence
<220> FEATURE:
<223> OTHER INFORMATION: the sequence is synthetized

<400> SEQUENCE: 13
ggtaacggta gagtgctgca tagccgggat agag                                34

<210> SEQ ID NO 14
<211> LENGTH: 24
<212> TYPE: DNA
<213> ORGANISM: Artificial Sequence
<220> FEATURE:
<223> OTHER INFORMATION: the sequence is synthetized

```
<400> SEQUENCE: 14
tatccgtccg gcgtctggtg accc                                              24

<210> SEQ ID NO 15
<211> LENGTH: 24
<212> TYPE: DNA
<213> ORGANISM: Artificial Sequence
<220> FEATURE:
<223> OTHER INFORMATION: the sequence is synthetized

<400> SEQUENCE: 15
gggtcaccag acgccggacg gata                                              24

<210> SEQ ID NO 16
<211> LENGTH: 33
<212> TYPE: DNA
<213> ORGANISM: Artificial Sequence
<220> FEATURE:
<223> OTHER INFORMATION: the sequence is synthetized

<400> SEQUENCE: 16
gttgttatcc gtccgaattc tggtgacccg ccg                                    33

<210> SEQ ID NO 17
<211> LENGTH: 33
<212> TYPE: DNA
<213> ORGANISM: Artificial Sequence
<220> FEATURE:
<223> OTHER INFORMATION: the sequence is synthetized

<400> SEQUENCE: 17
cggcgggtca ccagaattcg gacggataac aac                                    33

<210> SEQ ID NO 18
<211> LENGTH: 36
<212> TYPE: DNA
<213> ORGANISM: Artificial Sequence
<220> FEATURE:
<223> OTHER INFORMATION: the sequence is synthetized

<400> SEQUENCE: 18
gttgttatcc gtccggaatc tggtgacccg ccgttc                                 36

<210> SEQ ID NO 19
<211> LENGTH: 36
<212> TYPE: DNA
<213> ORGANISM: Artificial Sequence
<220> FEATURE:
<223> OTHER INFORMATION: the sequence is synthetized

<400> SEQUENCE: 19
gaacggcggg tcaccagatt ccggacggat aacaac                                 36

<210> SEQ ID NO 20
<211> LENGTH: 38
<212> TYPE: DNA
<213> ORGANISM: Artificial Sequence
<220> FEATURE:
<223> OTHER INFORMATION: the sequence is synthetized

<400> SEQUENCE: 20
gttcgtgtta tccagggtaa tggtgttaac gctgactc                               38

<210> SEQ ID NO 21
```

```
<211> LENGTH: 38
<212> TYPE: DNA
<213> ORGANISM: Artificial Sequence
<220> FEATURE:
<223> OTHER INFORMATION: the sequence is synthetized

<400> SEQUENCE: 21
gagtcagcgt taacaccatt accctggata acacgaac                              38

<210> SEQ ID NO 22
<211> LENGTH: 30
<212> TYPE: DNA
<213> ORGANISM: Artificial Sequence
<220> FEATURE:
<223> OTHER INFORMATION: the sequence is synthetized

<400> SEQUENCE: 22
gttatccagg gtgaaggtgt taacgctgac                                       30

<210> SEQ ID NO 23
<211> LENGTH: 30
<212> TYPE: DNA
<213> ORGANISM: Artificial Sequence
<220> FEATURE:
<223> OTHER INFORMATION: the sequence is synthetized

<400> SEQUENCE: 23
gtcagcgtta acaccttcac cctggataac                                       30

<210> SEQ ID NO 24
<211> LENGTH: 27
<212> TYPE: DNA
<213> ORGANISM: Artificial Sequence
<220> FEATURE:
<223> OTHER INFORMATION: the sequence is synthetized

<400> SEQUENCE: 24
cacccgcacc gtgcgaccca gaaattc                                          27

<210> SEQ ID NO 25
<211> LENGTH: 27
<212> TYPE: DNA
<213> ORGANISM: Artificial Sequence
<220> FEATURE:
<223> OTHER INFORMATION: the sequence is synthetized

<400> SEQUENCE: 25
gaatttctgg gtcgcacggt gcgggtg                                          27

<210> SEQ ID NO 26
<211> LENGTH: 35
<212> TYPE: DNA
<213> ORGANISM: Artificial Sequence
<220> FEATURE:
<223> OTHER INFORMATION: the sequence is synthetized

<400> SEQUENCE: 26
gcaacacccg caccgtaata cccagaaatt cgctc                                 35

<210> SEQ ID NO 27
<211> LENGTH: 35
<212> TYPE: DNA
<213> ORGANISM: Artificial Sequence
<220> FEATURE:
<223> OTHER INFORMATION: the sequence is synthetized

<400> SEQUENCE: 27
```

```
gagcgaattt ctgggtatta cggtgcgggt gttgc                              35

<210> SEQ ID NO 28
<211> LENGTH: 26
<212> TYPE: DNA
<213> ORGANISM: Artificial Sequence
<220> FEATURE:
<223> OTHER INFORMATION: the sequence is synthetized

<400> SEQUENCE: 28
cccgcaccgt gaaacccaga aattcg                                        26

<210> SEQ ID NO 29
<211> LENGTH: 26
<212> TYPE: DNA
<213> ORGANISM: Artificial Sequence
<220> FEATURE:
<223> OTHER INFORMATION: the sequence is synthetized

<400> SEQUENCE: 29
cgaatttctg ggtttcacgg tgcggg                                        26
```

NICOTINAMIDE PHOSPHORIBOSYLTRANSFERASE (NAMPT) MUTANT AND USE THEREOF

CROSS REFERENCE TO RELATED APPLICATIONS

This application is the national phase entry of International Application No. PCT/CN2016/092456, filed on Jul. 30, 2016, the entire contents of which are incorporated herein by reference.

TECHNICAL FIELD

The present invention relates to technical field of molecular biology and biotechnology, and particularly a nicotinamide phosphoribosyltransferase (Nampt) mutant artificially obtained through Site-directed mutagenesis.

BACKGROUND OF THE INVENTION

Nampt, also known as visfatin or pre-B cell colony enhancer factor (PBEF), is a protein indispensable for the life activities of mammalians that is widely distributed in various tissues, particularly in adipose tissue, liver, muscle and bone marrow of human.

At present, Nampt is considered to have mainly the following 3 functions, 1. Nampt functions to have an enzyme activity, by which nicotinamide and 5'-phosphoribosyl-1'-pyrophosphate (PRPP) are catalyzed to convert into nicotinamide mononucleotide (NMN) and pyrophosphate, and NMN is then catalytically converted, by nicotinamide mononucleotide adenylyltransferase (Nmnat), into nicotinamide adenine dinucleotide (NAD), a energy substance essential to the cells. 80% of NAD in the mammalian cells is synthesized through this biosynthetic pathway, and Nampt is the rate limiting enzyme of the pathway, thus regulating the intracellular level of NAD. 2. Nampt functions as a pre-B cell colony enhancer factor (PBEF) secreted by lymphocytes, which stimulates the formation of B cell precursors in the presence of Interleukin7 (IL-7) and stem cell factor (SCF). 3. Nampt functions as an adipokine secreted by adipose cells and is involved in various biological functions. In 2005, Fukuhara et al. found that Nampt can activate the insulin receptor signaling by direct interaction with the insulin receptor. Since Nampt is highly expressed in visceral adipocytes, it is referred to as Visfatin.

With the increasing insight into the medicinal and health care effects of NMN, the market demand for NMN grows increasingly. The most environmentally friendly and pollution free method for producing NMN is a biocatalytic method in which nicotinamide and 5'-phosphoribosyl-1'-pyrophosphate (PRPP) are catalytically converted into NMN by Nampt. However, due to the low enzyme activity of the existing wild-type Nampt, the yield is low when Nampt is used in large-scale industrial catalytic production of NMN. As a result, the production cost is high, and the product is less competitive in the market, which severely restrict the industrial application of the biocatalytic production technology of NMN.

Therefore, increasing the catalytic activity of Nampt is a key factor in reducing the biocatalytic synthesis cost of NMN, increasing the industrial application value of Nampt, and promoting the application of biocatalytic technology in industrial production of NMN.

SUMMARY OF THE INVENTION

In view of the problems of low catalytic activity and low industrial application value of the existing Nampt mentioned in the background art, an object of the present invention is to provide a Nampt mutant having a catalytic activity which is higher than that of a conventional wild type parent, by which nicotinamide and PRPP are efficiently catalyzed to convert into NMN, thus greatly reducing the cost for biocatalytic production of NMN in the industry. Therefore, the mutant has a high industrial application value.

In order to achieve the above object, site-directed mutagenesis is made by the present inventors to the gene of parent Nampt having a nucleotide sequence as shown in SEQ ID NO: 1, and the gene is then amplified by PCR, inserted into an appropriate vector, and then screened in an LB medium, to obtain a series of Nampt mutants having high catalytic activity. Accordingly, the present invention provides a Nampt mutant, which is a protein of (a) or (b) shown below:

(a) a protein having an amino acid sequence a shown in SEQ ID NO: 3; and (b) a protein derived from (a) by substitution, deletion, or insertion of one or more amino acids in the amino acid sequence as defined in (a), and having Nampt catalytic activity for the substrates nicotinamide and PRPP that is higher than the parent having an amino acid sequence as shown in SEQ ID NO: 2.

The parent as used herein refers to Nampt derived from *Meiothermus ruber* DSM 1279, the nucleotide sequence is as shown in SEQ ID NO: 1 and the amino acid sequence is as shown in SEQ ID NO: 7.

Preferably, the mutant has at least one mutation at at least one position selected from positions 180, 182, 231, 298, 338, and 377, compared with the amino acid sequence as shown in SEQ ID NO: 2.

More preferably, the mutant has at least one of the mutations F180A, F 180W, A182Y E231A, E231Q, D298A, D298N, D298E, D338N, D338E, D377A, D377N, and D377E.

The present invention further provides a nucleotide sequence encoding the Nampt mutant.

The present invention further provides an expression vector comprising the nucleotide sequence.

The present invention further provides a viable cell transformed with the nucleotide sequence and capable of expressing and secreting the Nampt mutant.

The present invention further provides use of the Nampt mutant in a process for preparing nicotinamide mononucleotide, where the process may be a biocatalytic process or a fermentation process.

The biocatalytic process for the preparation of nicotinamide mononucleotide (NMN) described above specifically refers to a process in which the substrates are catalyzed to convert into NMN by a biological enzyme, where the biological enzymes is the Nampt mutant according to the present invention or a combination of the Nampt mutant according to the present invention with one or more other enzymes; the substrates may be PRPP and nicotinamide or precursors able to be converted into PRPP or nicotinamide.

For example, nicotinamide and PRPP are used as raw materials for catalytically preparing NMN in the presence of the Nampt mutant of the present invention;

nicotinamide ATP, and xylose are used as raw materials for catalytically preparing NMN in the presence of the Nampt mutant of the present invention, ribose phosphate pyrophosphokinase, ribose-5-phosphate isomerase, ribulose-3-phosphate isomerase, xylulose kinase and xylose isomerase;

nicotinamide, ATP, and ribose are used as raw materials for catalytically preparing NMN in the presence of the Nampt mutant of the present invention, ribose phosphate pyrophosphokinase, and ribokinase;

nicotinamide, pyrophosphate or a salt thereof and AMP are used as raw materials for catalytically preparing NMN in the presence of the Nampt mutant of the present invention and adenine phosphoribosyltransferase;

nicotinamide, ATP, and AMP are used as raw materials for catalytically preparing NMN in the presence of the Nampt mutant of the present invention, ribose phosphate pyrophosphokinase, and AMP nucleosidase; and nicotinamide, pyrophosphate or a salt thereof and inosinic acid or a salt thereof are used as raw materials for catalytically preparing NMN in the presence of the Nampt mutant of the present invention, hypoxanthine phosphoribosyltransferase, and xanthine oxidase.

Preferably, the Nampt mutant of the present invention is used in the form of an enzyme solution, an enzyme lyophilized powder, enzyme-containing cells, an immobilized enzyme, or immobilized enzyme-containing cells.

Beneficial Effect:

Compared with the existing wild-type Nampt, the Nampt mutant provided in the present invention has a considerably increased enzymatic activity. As shown in an enzyme activity assay with nicotinamide and PRPP as substrates, the enzymatic activity of the Nampt mutant provided in the present invention is 1.2-6.9 times of the enzymatic activity of the parent. Such a high catalytic activity allows the mutant to be used in the form of a crude enzyme without purification or be used merely after partial purification. This results in a greatly reduced cost in the catalytic production of NMN by using the Nampt mutant provided in the present invention, thus bringing about high market competitiveness, and enabling the method for producing NMN by biocatalysis to be applicable to large-scale industrial production.

DETAILED DESCRIPTION OF THE INVENTION

The present invention will be described in further detail with reference to specific examples. The following examples are illustrative of the present invention and the present invention is not limited thereto. Where no specific conditions are given in the examples, conventional conditions or conditions recommended by a manufacturer are adopted.

A process for preparing the Nampt mutant provided in the present invention was substantially as follows. A plasmid vector containing parent Nampt gene was constructed. Then a site for site-directed mutation and the type of the amino acid after mutation were determined. Suitable primers were synthesized, DNA fragments were amplified by PCR using the plasmid vector containing parent Nampt gene as a template, the amplified DNA fragments were assembled, and the full-length mutant gene was amplified by PCR. Then, the full-length mutant gene was cloned onto a suitable vector, then transformed into suitable host cells, and incubated, to screen out positive clones having Nampt activity. Plasmid DNA was extracted from the positive clones, and sequenced, to determine the mutation introduced. After a fragment of interest is determined to be inserted into the vector, the clones were screened in a LB+ Kanamycin medium, to obtain a series of Nampt mutants having high catalytic activity.

In the preparation method, any suitable vectors may be used, for example, prokaryotic expression vectors such as pRSET, pES21, and the like; and cloning vectors such as pUC18/19 and pBluescript-SK. In the present invention, pRSET-A is preferably used as a vector. The host cell to which the vector is transferred may be a prokaryotic cell including *Escherichia coli* or an eukaryotic cell including *Saccharomyces cerevisiae* and *Pichia pastoris*.

For the enzymes used in the following examples, except that the Nampt mutant is obtained through artificially induced site-directed mutation of patent Nampt gene derived from Meiothermus ruler DSM 1279 and having a nucleotide sequence as shown in SEQ ID NO:1, the remaining enzymes are all enzyme lyophilized powders directly purchased from the market.

EXAMPLE 1

Construction of Plasmid Vector Containing Parent Nampt Gene

Whole sequence artificial synthesis was performed on the parent Nampt gene sequence publicized in the Genebank (GenBank Accession No.: CP001743.1) derived from Meiothermus ruber DSM 1279 (by a commercial synthesis company). The synthesized product was enzymatically cleaved by the restriction endonucleases NdeI and BamHI, and then ligated to the vector pRSET-A (available from Invitrogen. USA) that was also enzymatically cleaved by the restriction endonucleases NdeI and BamHI , to obtain plasmid pRSET-nampt. After DNA sequencing, it is determined that the nucleotide sequence of the cloned parent Nampt gene is as shown in SEQ ID NO: 1, and the amino acid sequence is as shown in SEQ ID NO: 2.

EXAMPLE 2

Preparation of Nampt Mutants

PCR amplification reaction system: 20 mM Tris-HCI (pH 8.8), 10 mM KCI, 10 mM (NH4)2SO4, 2 mM MgSO4, 0.1% Triton X-100, 50 mM dATP, 50 mM dTTP, 50 mM dCTP, 50 mM dGTP, 1.5 Pfu DNA polymerase (Promega, USA), 20 ng DNA template, and 400 nM upstream primer, and 400nM downstream primer, where the reaction volume was adjusted to 50 µl with sterile water.

PCR amplification reaction conditions: 3 min at 95 ° C.; 35 cycles of: 50 s at 95 °C., 30 s at 52 ° C., and 3 min at 72 ° C.; and finally 5 min at 72 ° C.

1. Preparation of F180A Mutant

The primer pair F180A-F: 540 GTTCAAACTGCACGACGCGGGTGCTCGTGGTGTTTC 3' (SEQ ID NO: 4) and F180A-R: 5' GAAACACCACGAGCACCCGCGTCGTGCAGTTTGAAC 3' (SEQ ID NO: 5) were used. The plasmid pRSET-nampt constructed in Example 1 was used as a template. The F180A mutant gene was amplified by high-fidelity PCR using the above PCR amplification reaction system and PCR amplification reaction conditions. The amplified product was isolated by electrophoresis on 1% agarose gel, recovered using a commercial kit, and ligated to the vector pRSET-A (See Example 1 for details) to obtain plasmid pRSET-F180A. The plasmid pRSET-F180A was transformed into competent bacterial cells *E. coli* BL21, and clones having Nampt activity were screened out on a Luria broth (LB) plate (containing 50 mg/L Kanamycin). Plasmid pRSET-F180A DNA was extracted from the clones, and sequenced to determine that the point mutation introduced was correct. Compared with the parent amino acid sequence as shown in SEQ ID NO: 2, the amino acid sequence of the F180A mutant is as shown in SEQ ID NO: 3 and has a mutation of Phe (F) to Ala (A) at position 180.

2. Preparation of F180W Mutant The primer pair F180W-F: 5' GTTCAAACTGCACGACTGGGGGTGCTCGTGGT- GTTTC 3' (SEQ ID NO: 6) and F180W-R: 5' GAAACAC-CACGAGGACCCCAGTCGTGCAGTTTGAAC 3' (SEQ ID NO: 7) were used. The plasmid pRSET-nampt constructed in Example 1 was used as a template. The F 180W mutant gene was amplified by high-fidelity PCR using the above PCR amplification reaction system and PCR amplification reaction conditions. The amplified product was isolated by electrophoresis on 1% agarose gel, recovered using a commercial kit, and ligated to the vector pRSET-A (See Example 1 for details) to obtain plasmid pRSET-F180W. The plasmid pRSET-F180W was transformed into competent bacterial cells E. coli BL21, and clones having Nampt activity were screened out on a Luria broth (LB) plate (containing 50 mg/L Kanamycin). Plasmid pRSET-F 180W DNA was extracted from the clones, and sequenced to determine that the point mutation introduced was correct. Compared with the parent amino acid sequence as shown in SEQ ID NO: 2, the amino acid sequence of the F 180W mutant has a mutation of Phe (F) to Trp (W) at position 180.

3. Preparation of A182Y Mutant

The primer pair A182Y-F: 5' CAAACTGCACGACT-TCGGTTATCGTGGTGTTTCTTCTCTG 3' (SEQ ID NO: 8) and A182Y-R: 5' CAGAGAAGAAACACCACGA-TAACCGAAGTCGTGCAGTTTG 3' (SEQ ID NO: 9) were used. The plasmid pRSET-nampt constructed, in Example 1 was used as a template. The A182Y mutant gene was amplified by high-fidelity PCR using the above PCR amplification reaction system and PCR amplification reaction conditions. The amplified product was isolated by electrophoresis on 1% agarose gel, recovered using a commercial kit, and ligated to the vector pRSET-A (See Example 1 for details) to obtain plasmid pRSET-A182Y. The plasmid pRSET-A182Y was transformed into competent bacterial cells E. coli BL21, and clones having Nampt activity were screened out on a Luria broth (LB) plate (containing 50 mg/L Kanamycin). Plasmid pRSET-A182Y DNA was extracted from the clones, and sequenced to determine that the point mutation introduced was correct. Compared with the parent amino acid sequence as shown in SEQ ID NO: 2, the amino acid sequence of A182Y mutant has a mutation of Ala (A) to Tyr (Y) at position 182.

4. Preparation of E231A Mutant

The primer pair E231A-F: 5' CTATCCCGGCTATGGCG-CACTCTACCGTTAC 3' (SEQ ID NO: 10) and E231A-R: 5' GTAACGGTAGAGTGCGCCATAGCCGGGATAG 3' (SEQ ID NO: 11) were used. The plasmid pRSET-nampt constructed in Example 1 was used as a template. The E231A mutant gene was amplified by high-fidelity PCR using the above PCR amplification reaction system and PCR amplification reaction conditions. The amplified product was isolated by electrophoresis on 1% agarose gel, recovered using a commercial kit, and ligated to the vector pRSET-A (See Example 1 for details) to obtain plasmid pRSET-E231A. The plasmid pRSET-E231A was transformed into competent bacterial cells E. coli BL21, and clones having Nampt activity were screened out on a Luria broth (LB) plate (containing 50 mg/L Kanamycin). Plasmid pRSET-E231A DNA was extracted from the clones, and sequenced to determine that the point mutation introduced was correct. Compared with the parent amino acid sequence as shown in SEQ ID NO: 2, the amino acid sequence of the E231A mutant has a mutation of Glu (E) to Ala (A) at position 231.

5. Preparation of E231Q Mutant

The primer pair E231Q-F: 5' CTCTATCCCGGCTAT-GCAGCACTCTACCGTTACC 3' (SEQ ID NO: 12) and E231Q-R: 5' GGTAACGGTAGAGTGCTGCATAGC-CGGGATAGAG 3' (SEQ ID NO: 13) were used. The plasmid pRSET-nampt constructed in Example 1 was used as a template. The E231Q mutant gene was amplified by high-fidelity PCR using the above PCR amplification reaction system and PCR amplification reaction conditions. The amplified product was isolated by electrophoresis on 1% agarose gel, recovered using a commercial kit, and ligated to the vector pRSET-A (See Example 1 for details) to obtain plasmid pRSET-E231Q. The plasmid pRSET-E231Q was transformed into competent bacterial cells E. coli BL21, and clones having Nampt activity were screened out on a Luria broth (LB) plate (containing 50 mg/L Kanamycin). Plasmid pRSET-E231Q DNA was extracted from the clones, and sequenced to determine that the point mutation introduced was correct. Compared with the parent amino acid sequence as shown in SEQ ID NO: 2, the amino acid sequence of E231Q mutant has a mutation of Glu (E) to Gln (Q) at position 231.

6. Preparation of D298A Mutant The primer pair D298A-F: 5' TATCCGTCCGGCGTCTGGTGACCC 3' (SEQ ID NO: 14) and D298A-R: 5' GGGTCACCAGACGCCG-GACGGATA 3' (SEQ ID NO: 15) were used. The plasmid pRSET-nampt constructed in Example 1 was used as a template. The D298A mutant gene was amplified by high-fidelity PCR using the above PCR amplification reaction system and PCR amplification reaction conditions. The amplified product was isolated by electrophoresis on 1% agarose gel, recovered using a commercial kit, and ligated to the vector pRSET-A (See Example 1 for details) to obtain plasmid pRSET-D298A. The plasmid pRSET-D298A was transformed into competent bacterial cells E. coli BL21, and clones having Nampt activity were screened out on a Luria broth (LB) plate (containing 50 mg/L Kanamycin). Plasmid pRSET-D298A DATA was extracted from the clones, and sequenced to determine that the point mutation introduced was correct. Compared with the parent amino acid sequence as shown in SEQ ID NO: 2, the amino acid sequence of the D298A mutant has a mutation of Asp (D) to Ala (A) at position 298.

7. Preparation of D298N Mutant

The primer pair D298N-F: 5' GTTGTTATCCGTC-CGAATTCTGGTGACCCGCCG 3' (SEQ ID NO: 16) and D298N-R: 5' CGGCGGGTCACCAGAATTCGGACGGA-TAACAAC 3' (SEQ ID NO: 17) were used. The plasmid pRSET-nampt constructed in Example 1 was used as a template. The D298N mutant gene was amplified by high-fidelity PCR using the above PCR amplification reaction system and PCR amplification reaction conditions. The amplified product was isolated by electrophoresis on 1% agarose gel, recovered using a commercial kit, and ligated to the vector pRSET-A (See Example 1 for details) to obtain plasmid pRSET-D298N. The plasmid pRSET-D 298N was transformed into competent bacterial cells E. coli BL21, and clones having Nampt activity were screened out on a Luria broth (LB) plate (containing 50 mg/L Kanamycin). Plasmid pRSET-D298N DNA was extracted from the clones, and sequenced to determine that the point mutation introduced was correct. Compared with the parent amino acid sequence as shown in SEQ ID NO: 2, the amino acid sequence of the D298N mutant has a mutation of Asp (D) to Asn (N) at position 298.

8. Preparation of D298E Mutant

The primer pair D298E-F: GTTGTTATCCGTCCG-GAATCTGGTGACCCGCCGTTC 3' (SEQ ID NO: 18) and D298E-F: 5' GAACGGCGGGTCACCAGATTCCG-GACGGATAACAAC 3' (SEQ ID NO: 19) were used. The plasmid pRSET-nampt constructed in Example 1 was used as a template. The D298E mutant gene was amplified by high-fidelity PCR using the above PCR amplification reaction system and PCR amplification reaction conditions. The amplified product was isolated by electrophoresis on 1% agarose gel, recovered using a commercial kit, and ligated to the vector pRSET-A (See Example 1 for details) to obtain plasmid pRSET-D298E. The plasmid pRSET-D298E was transformed into competent bacterial cells *E. coli* BL21, and clones having Nampt activity were screened out on a Luria broth (LB) plate (containing 50 mg/L Kanamycin). Plasmid pRSET-D298E DNA was extracted from the clones, and sequenced to determine that the point mutation introduced was correct. Compared with the parent amino acid sequence as shown in SEQ ID NO: 2, the amino acid sequence of the D298E, mutant has a mutation of Asp (D) to Glu (E) at position 298.

9. Preparation of D338N Mutant

The primer pair D338N-F: 5' GTTCGTGTTATCCA-GGGTAATGGTGTTAACGCTGACTC 3' (SEQ ID NO: 20) and D338N-R: 5' GAGTCAGCGTTAACACCATTAC-CCTGGATAACACGAAC 3' (SEQ ID NO: 21) were used. The plasmid pRSET-nampt constructed in Example 1 was used as a template. The D338N mutant gene was amplified by high-fidelity PCR using the above PCR amplification reaction system and PCR amplification reaction conditions. The amplified product was isolated by electrophoresis on 1% agarose gel, recovered using a commercial kit, and ligated to the vector pRSET-A (See Example 1 for details) to obtain plasmid pRSET-D338N. The plasmid pRSET-D338N was transformed into competent bacterial cells *E. coli* BL21, and clones having Nampt activity were screened out on a Luria broth (LB) plate (containing 50 mg/L Kanamycin). Plasmid pRSET-D338N DNA was extracted from the clones, and sequenced to determine that the point mutation introduced was correct. Compared with the parent amino acid sequence as shown in SEQ ID NO: 2, the amino acid sequence of the D338N mutant has a mutation of Asp (D) to Asn (N) at position 338.

10. Preparation of D338E Mutant

The primer pair D338E-F: 5' GTTATCCAGGGT-GAAGGTGTTAACGCTGAC 3' (SEQ ID NO: 22) and D338E-R: 5' GTCAGCGTTAACACCTTCACCCTGGA-TAAC 3' (SEQ ID NO: 23) were used. The plasmid pRSET-nampt constructed in Example 1 was used as a template. The D338E mutant gene was amplified by high-fidelity PCR using the above PCR amplification reaction system and PCR amplification reaction conditions. The amplified product was isolated by electrophoresis on 1% agarose gel, recovered using a commercial kit, and ligated to the vector pRSET-A (See Example 1 for details) to obtain plasmid pRSET-D338E. The plasmid pRSET-D338E was transformed into competent bacterial cells *E. coli* BL21, and clones having Nampt activity were screened out on a Luria broth (LB) plate (containing 50 mg/L Kanamycin). Plasmid pRSET-D338E DNA was extracted from the clones, and sequenced to determine that the point mutation introduced was correct. Compared with the parent amino acid sequence as shown in SEQ ID NO: 2, the amino acid sequence of the D338E, mutant has a mutation of Asp (D) to Glu (E) at position 338.

11. Preparation of D377A Mutant

The primer pair D377A-F: 5' CACCCGCACCGTGC-GACCCAGAAATTC 3' (SEQ ID NO: 24) and D377A-R: 5' GAATTTCTGGGTCGCACGGTGCGGGTG 3' (SEQ ID NO: 25) were used. The plasmid pRSET-nampt constructed in Example 1 was used as a template. The D377A mutant gene was amplified by high-fidelity PCR using the above PCR amplification reaction system and PCR amplification reaction conditions. The amplified product was isolated by electrophoresis on 1% agarose gel, recovered using a commercial kit, and ligated to the vector pRSET-A (See Example 1 for details) to obtain plasmid pRSET-D377A. The plasmid pRSET-D377A was transformed into competent bacterial cells *E. coli* BL21, and clones having Nampt activity were screened out on a Luria broth (LB) plate (containing 50 mg/L Kanamycin). Plasmid pRSET-D377A DNA was extracted from the clones, and sequenced to determine that the point mutation introduced was correct. Compared with the parent amino acid sequence as shown in SEQ ID NO: 2, the amino acid sequence of the D377A mutant has a mutation of Asp (D) to Ala (A) at position 377.

12. Preparation of D377N Mutant

The primer pair D377N-F: 5' GCAACACCCGCACCG-TAATACCCAGAAATTCGCTC 3' (SEQ ID NO: 26) and D377N-R: 5' GAGCGAATTTCTGGGTATTACGGT-GCGGGTGTTGC 3' (SEQ ID NO: 27) were used. The plasmid pRSET-nampt constructed in Example 1 was used as a template. The D377N mutant gene was amplified by high-fidelity PCR using the above PCR amplification reaction system and PCR amplification reaction conditions. The amplified product was isolated by electrophoresis on 1% agarose gel, recovered using a commercial kit, and ligated to the vector pRSET-A (See Example 1 for details) to obtain plasmid pRSET-D377N. The plasmid pRSET-D377N was transformed into competent bacterial cells *E. coli* BL21, and clones having Nampt activity were screened out on a Luria broth (LB) plate (containing 50 mg/L Kanamycin). Plasmid pRSET-D377N DNA was extracted from the clones, and sequenced to determine that the point mutation introduced was correct. Compared with the parent amino acid sequence as shown in SEQ ID NO: 2, the amino acid sequence of the D377N mutant has a mutation of Asp (D) to Asn (N) at position 377.

13. Preparation of D377E Mutant

The primer pair D377E-F: 5' CCCGCACCGTGAAAC-CCAGAAATTCG 3' (SEQ ID NO: 28) and D377E-R: 5' CGAATTTCTGGGTTTCACGGTGCGGG 3' (SEQ ID NO: 29) were used. The plasmid pRSET-nampt constructed in Example 1 was used as a template. The D377E mutant gene was amplified by high-fidelity PCR using the above PCR amplification reaction system and PCR amplification reaction conditions. The amplified product was isolated by electrophoresis on 1% agarose gel, recovered using a commercial kit, and ligated to the vector pRSET-A (See Example 1 for details) to obtain plasmid pRSET-D377E. The plasmid pRSET-D377E was transformed into competent bacterial cells *E. coli* BL21, and clones having Nampt activity were screened out on a Luria broth (LB) plate (containing 50 mg/L Kanamycin). Plasmid pRSET-D377E DNA was extracted from the clones, and sequenced to determine that the point mutation introduced was correct. Compared with the parent amino acid sequence as shown in SEQ ID NO: 2, the amino acid sequence of the D377E mutant has a mutation of Asp (D) to Glu (E) at position 377.

14. Preparation of E231Q/D338E Mutant

The primer pair D338E-F: GTTATCCAGGGTGAAGGT-GTTAACGCTGAC 3' (SEQ ID NO: 22) and D338E-R: 5' GTCAGCGTTAACACCTTCACCCTGGATAAC 3' (SEQ ID NO: 23) were used. The plasmid pRSET-E231Q constructed in Section 5 in Example 2 was used as a template. The E231Q/D338E mutant gene was amplified by high-fidelity PCR using the above PCR amplification reaction system and PCR amplification reaction conditions. The amplified product was isolated by electrophoresis on 1% agarose gel, recovered using a commercial kit, and ligated to the vector pRSET-A (See Example 1 for details) to obtain plasmid pRSET-21. The plasmid pRSET-21 was transformed into competent bacterial cells *E. coli* BL21, and clones having Nampt activity were screened out on a Luria broth (LB) plate (containing 50 mg/L Kanamycin). Plasmid pRSET-21 DNA was extracted from the clone, and sequenced to determine that the point mutation introduced was correct. Compared with the parent amino acid sequence as shown in SEQ ID NO: 2, the amino acid sequence of the E231Q/D338E mutant has a mutation of Glu (E) to Gln (Q) at position 231, and a mutation of Asp (D) to Glu (E) at positron 338.

15. Preparation of E231Q/D377E Mutant

The primer pair D377E-F: 5' CCCGCACCGTGAAAC-CCAGAAATTCG 3' (SEQ ID NO: 28) and D377E-R: 5' CGAATTTCTGGGTTTCACGGTGCGGG 3' (SEQ ID NO: 29) were used. The plasmid pRSET-E231Q constructed in Section 5 in Example 2 was used as a template. The E231Q/D377E mutant gene was amplified by high-fidelity PCR using the above PCR amplification reaction system and PCR amplification reaction conditions. The amplified product was isolated by electrophoresis on 1% agarose gel, recovered using a commercial kit, and ligated to the vector pRSET-A (See Example 1 for details) to obtain plasmid pRSET22. The plasmid pRSET-22 was transformed into competent bacterial cells *E. coli* BL21, and clones having Nampt activity were screened out on a Luria broth (LB) plate (containing 50 mg/L Kanamycin). Plasmid pRSET-22 DNA was extracted from the clone, and sequenced to determine that the point mutation introduced was correct. Compared with the parent amino acid sequence as shown in SEQ ID NO: 2, the amino acid sequence of the E231Q/D377E mutant has a mutation of Glu (E) to Gln (Q) at position 231 and a mutation of Asp (D) to Glu (E) at position 377.

16. Preparation of D338E/D377E Mutant

The primer pair D377E-F: 5' CCCGCACCGTGAAAC-CCAGAAATTCG 3' (SEQ ID NO: 28) and D377E-R: 5' CGAATTTCTGGGTTTCACGGTGCGGG 3' (SEQ ID NO: 29) were used. The plasmid pRSET-D338E constructed in Section 10 in Example 2 was used as a template. The D338E/D377E mutant gene was amplified by high-fidelity PCR using the above PCR amplification reaction system and PCR amplification reaction conditions. The amplified product was isolated by electrophoresis on 1% agarose gel, recovered using a commercial kit, and ligated to the vector pRSET-A (See Example 1 for details) to obtain plasmid pRSET-23. The plasmid pRSET-23 was transformed into competent bacterial cells *E. coli* BL21, and clones having Nampt activity were screened out on a Luria broth (LB) plate (containing 50 mg/L Kanamycin). Plasmid pRSET-23 DNA was extracted from the clone, and sequenced to determine that the point mutation introduced was correct. Compared with the parent amino acid sequence as shown in SEQ ID NO: 2, the amino acid sequence of the D338E/D377E mutant has a mutation of Asp (D) to Glu (E) at position 338 and a mutation of Asp (D) to Glu (E) at position 377.

17. Preparation of E231Q/D338E/D377E Mutant

The primer pair D377E-F: 5' CCCGCACCGTGAAAC-CCAGAAATTCG 3' (SEQ ID NO: 28) and D377E-R: 5' CGAATTTCTGGGTTTCACGGTGCGGG 3' (SEQ ID NO: 29) were used. The plasmid pRSET-21 constructed in Section 14 in Example 2was used as a template. The E231Q/D338E/D377E mutant gene was amplified by high-fidelity PCR using the above PCR amplification reaction system and PCR amplification reaction conditions. The amplified product was isolated by electrophoresis on 1% agarose gel, recovered using a commercial kit, and ligated to the vector pRSET-A (See Example 1 for details) to obtain plasmid pRSET-31. The plasmid pRSET-31 was transformed into competent bacterial cells *E. coli* BL21, and clones having Nampt activity were screened out on a Luria broth (LB) plate (containing 50 mg/L Kanamycin). Plasmid pRSET-31 DNA was extracted from the clone, and sequenced to determine that the point mutation introduced was correct. Compared with the parent amino acid sequence as shown in SEQ ID NO: 2, the amino acid sequence of the E231Q/D338E/D377E mutant has a mutation of Glu (E) to Gln (Q) at position 231, a mutation of Asp (D) to Glu (E) at position 338, and a mutation of Asp (D) to Glu (E) at position 377.

18. Preparation of E231Q/D298A/D338E/D377E Mutant

The primer pair D298A-F: 5' TATCCGTCCG-GCGTCTGGTGACCC 3' (SEQ ID NO: 14) and D298A-R: 5' GGGTCACCAGACGCCGGACGGATA 3' (SEQ ID NO: 15) were used. The plasmid pRSET-31 constructed in Section 17 in Example 2 was used as a template. The E231Q/D298A/D338E/D377E mutant gene was amplified by high-fidelity PCR using the above PCR amplification reaction system and PCR amplification reaction conditions. The amplified product was isolated by electrophoresis on 1% agarose gel, recovered using a commercial kit, and ligated to the vector pRSET-A (See Example 1 for details) to obtain plasmid pRSET-41. The plasmid pRSET-41 was transformed into competent bacterial cells *E. coli* BL21, and clones having Nampt activity were screened out on a Luria broth (LB) plate (containing 50 mg/L Kanamycin). Plasmid pRSET-41 DNA was extracted from the clone, and sequenced to determine that the point mutation introduced was correct. Compared with the parent amino acid sequence as shown in SEQ ID NO: 2, the amino acid sequence of the E231Q/D298A/D338E/D377E mutant has a mutation of Glu (E) to Gln (Q) at position 231, a mutation of Asp (D) to Ala (A) at position 298, a mutation of Asp (D) to Glu (E) at position 338, and a mutation of Asp (D) to Glu (E) at position 377.

EXAMPLE 3

Extraction of Enzymes

The plasmid pRSET-nampt containing parent Nampt gene and the plasmid pRSET-F180A, pRSET-F180W, pRSET-A182Y, pRSET-E231A, pRSET-E231Q, pRSET-D298A, pRSET-D298N, pRSET-D298E, pRSET-D338N, pRSET-D338E, pRSET-D377A, pRSET-D377N, pRSET-D377E, pRSET-21, pRSET-22, pRSET-23, pRSET-31, and pRSET-41 containing Nampt mutant genes were respectively transformed into competent bacterial cells *E. coli* BL21, and incubated for 24 hrs on a Luria broth (LB) plate (containing 50 mg/L Kanamycin) at 37° C. Individual clones were inoculated in 50 ml of LB liquid medium (containing 50 mg/L Kanamycin), and incubated for 16-20 hrs at 30° C. The bacterial cells were collected by centrifugation, and the same amount of cells were weighed and suspended in a cell lysis buffer (pH 7.5) at a ratio of 1:4. The bacterial cells were ultrasonically lyzed. After centrifugation (4-10° C., 12000 rpm, 10 mm), the supernatant was collected, that is, the protein supernatant of parent Nampt and a series of Nampt mutants was obtained respectively, which could be used in the enzyme activity assay and in the preparation of NMN by biocatalysis.

EXAMPLE 4

Enzyme Activity Assay

A substrate solution containing 60 mM nicotinamide, 25 mM PRPP, 18 mM $MgCl_2$, 15 mM KCl, and 100 mM Tris buffer was formulated and adjusted to pH 7.5. 19 portions of the substrate solution (each 900 μl) were taken, then added respectively to 100 μl of equal concentration of the protein supernatant of parent Nampt and a series of Nampt mutants obtained in Example 3, and reacted for 10 min at 37° C. The reaction was terminated by adding 100 μL of 25% trichloroacetic acid. The NMN content in the reaction solution was determined by HPLC, and the specific activity of each enzyme was calculated. Where the specific activity of parent Nampt was assumed to be 100, the relative specific activity of the parent and the mutants are as shown in Table 1.

TABLE 1

Enzyme activity of Nampt

| Name of enzyme | Relative specific activity |
|---|---|
| Parent | 100 |
| F180A mutant | 118 |
| F180W mutant | 122 |
| A182Y mutant | 187 |
| E231A mutant | 221 |
| E231Q mutant | 529 |
| D298A mutant | 236 |
| D298N mutant | 238 |
| D298E mutant | 149 |
| D338N mutant | 194 |
| D338E mutant | 516 |
| D377A mutant | 204 |
| D377N mutant | 279 |
| D377E mutant | 274 |
| E231Q/D338E mutant | 593 |
| E231Q/D377E mutant | 546 |
| D338E/D377E mutant | 601 |
| E231Q/D338E/D377E mutant | 654 |
| E231Q/D298A/D338E/D377E mutant | 691 |

EXAMPLE 5

Preparation of Nicotinamide Mononucleotide

A substrate solution containing 30 mM nicotinamide, 20 mM ATP, 30 mM xylose, 12 mM $MgCl_2$, 10 mM KCl, 10 mM $ZnCl_2$, and 100 mM Tris-HCl buffer was added to a reactor, and adjusted to pH 7.0-7.5. Then, various catalytic enzymes were added, in amounts of 10 ml of the protein supernatant of Nampt mutant (F180A) prepared in Example 3/L of substrate solution, 6 g of ribose phosphate pyrophosphokinase/L of substrate solution, 10 g of ribose-5-phosphate isomerase/L of substrate solution, 11 g of ribulose-3-phosphate isomerase/L of substrate solution, 10 g of xylulose kinase/L of substrate solution, 10 g of xylose isomerase/L of substrate solution. The system was stirred until uniform and then reacted. During the reaction process, stirring was continued (at a stirring speed of 50 rpm), the reaction temperature was controlled at 37° C., and the pH was maintained at 7.0-7.5. After 6 hrs of reaction, a crude nicotinamide mononucleotide product solution (containing 10 mM NMN) was obtained, which was filtered, purified, and dried, to obtain nicotinamide mononucleotide.

EXAMPLE 6

Preparation of Nicotinamide Mononucleotide

A substrate solution containing 30 mM nicotinamide, 20 mM ATP, 30 mM ribose, 15 mM $MgCl_2$, 15 mM KCl, and 100 mM Tris-HCl buffer was added to a reactor, and adjusted to pH 7.0-7.5. Then, various catalytic enzymes were added to the substrate solution in amounts of 10 ml of the protein supernatant of Nampt mutant (F180A) prepared in Section III of Example 6/L of substrate solution, 20 g of ribose phosphate pyrophosphokinase/L of substrate solution, and 20 g ribokinase/L of substrate solution. The system was stirred until uniform and then reacted. During the reaction process, stirring was continued (at a stirring speed of 50 rpm), the reaction temperature was controlled at 37° C., and the pH was maintained at 7.0-7.5. After 4 hrs of reaction, a crude nicotinamide mononucleotide product solution (containing 10 mM NMN) was obtained, which was filtered, purified, and dried, to obtain a product nicotinamide mononucleotide.

EXAMPLE 7

Preparation of Nicotinamide Mononucleotide

A substrate solution containing 75 mM nicotinamide, 75 mM disodium pyrophosphate, 50 mM AMP, 15 mM $MgCl_2$, 10 mM KCl, and 100 mM Tris-HCl buffer was added to a reactor, and adjusted to pH 7.0-7.5. Then, various catalytic enzymes were added in amounts of: 10 ml of the protein supernatant of Nampt mutant (F180A) prepared in Section III of Example 6/L of substrate solution, and 20 g of adenine phosphoribosyltransferase/L of substrate solution. The system was stirred until uniform and then reacted. During the reaction process, stirring was continued (at a stirring speed of 50 rpm), the reaction temperature was controlled at 37° C., and the pH was maintained at 7.0-8.0. After 5 hrs of reaction, a crude nicotinamide mononucleotide product solution (containing 49.6 mM NMN) was obtained, which was filtered, purified, and dried, to obtain a product nicotinamide mononucleotide.

EXAMPLE 8

Preparation of Nicotinamide Mononucleotide

A substrate solution containing 60 mM nicotinamide 10 mM ATP, 20 mM AMP, 15 mM $MgCl_2$, 15 mM KCl, and 100 mM Tris-HCl buffer was added to a reactor, and adjusted to pH 7.0-7.5. Then, various catalytic enzymes were added to the substrate solution in amounts of 10 ml of the protein supernatant of Nampt mutant (F180A) prepared in Section III of Example 6/L of substrate solution, 15 g of ribose phosphate pyrophosphokinase/L of substrate solution, and 15 g of AMP nucleosidase/L of substrate solution. The system was stirred until uniform and then reacted. During the reaction process, stirring was continued (at a stirring speed of 50 rpm), the reaction temperature was controlled at 37° C., and the pH was maintained at 7.0-7.5. After 3 hrs of reaction, a crude NMN product solution (containing 9.8 mM NMN) was obtained, which was filtered, purified, and dried, to obtain a product NMN.

EXAMPLE 9

Preparation of Nicotinamide Mononucleotide

A substrate solution containing 60 mM nicotinamide, 30 mM disodium pyrophosphate, 20 mM disodium inosinate, 20 mM MgCl$_2$, 20 mM ZuCl$_2$, 35 mM sodium bisulfite and 100 mM Tris-HCl buffer was added to a reactor, and adjusted to pH 7.0-7.5. Then, various catalytic enzymes were added to the substrate solution in amounts of: 10 ml of the protein supernatant of Nampt mutant (F180A) prepared in Section III of Example 6/L of substrate solution/L of substrate solution, 10 g of hypoxanthine phosphoribosyl-transferase/L of substrate solution, 20 g of xanthine oxidase/L of substrate solution. The system was stirred until uniform and then reacted. During the reaction process, stirring was continued (at a stirring speed of 50 rpm), the reaction temperature was controlled at 37° C., and the pH was maintained at 7.0-7.5. After 5 hrs of reaction, a crude nicotinamide mononucleotide product solution (containing 19.8 mM NMN) was obtained, which was filtered purified, and dried, to obtain a product nicotinamide mononucleotide.

What is claimed is:

1. A nicotinamide phosphoribosyltransferase (Nampt) mutant, wherein the Nampt mutant is a protein having the amino acid sequence of SEQ ID NO: 3.

2. An expression vector comprising a polynucleotide encoding a Nampt mutant, wherein the Nampt mutant is a protein having the amino acid sequence of SEQ ID NO: 3.

3. A viable cell, wherein the viable cell is transformed with a polynucleotide encoding a Nampt mutant, wherein the Nampt mutant is a protein having the amino acid sequence of SEQ ID NO: 3, and wherein the viable cell is capable of expressing and secreting the Nampt mutant.

* * * * *